United States Patent
Kim et al.

(10) Patent No.: US 6,716,857 B2
(45) Date of Patent: Apr. 6, 2004

(54) TETRAHYDROPYRIDINE DERIVATIVES ACTING ON MUSCARINIC ACETYLCHOLINE RECEPTORS

(75) Inventors: Youseung Kim, Seoul (KR); Soon Bang Kang, Uijeongbu-si (KR); Gyochang Keum, Seoul (KR); Min Seok Jang, Seoul (KR); Jae Yang Kong, Daejeon (KR); Dae Young Jeong, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/273,630

(22) Filed: Oct. 18, 2002

(65) Prior Publication Data

US 2003/0119880 A1 Jun. 26, 2003

(30) Foreign Application Priority Data

Oct. 27, 2001 (KR) ........................................ 2001-66568

(51) Int. Cl.⁷ ........................ A61K 31/44; C07D 401/04
(52) U.S. Cl. ..................................... 514/343; 546/278.4
(58) Field of Search ........................ 514/343; 546/278.4

(56) References Cited

U.S. PATENT DOCUMENTS 5,854,277 A * 12/1998 Kluender et al. ........... 514/448
5,859,047 A * 1/1999 Kluender et al. ........... 514/423

* cited by examiner

*Primary Examiner*—D. Margaret Seaman
(74) *Attorney, Agent, or Firm*—Jones Day

(57) ABSTRACT

The present invention relates to novel tetrahydropyridine derivatives of formula 1 having an appropriately substituted pyrrolidinone and oxime,

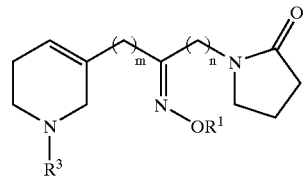

1 wherein m is 0 or 1, n is 1 or 2, $R^1$ is hydrogen, $C_{1-4}$ alkyl, $C_{2-4}$ alkynyl or aryl, $R^3$ is $C_{1-4}$ alkyl, which show high efficacy, low cholinergic adverse effects and high affinity for muscarinic acetylcholine receptor; and pharmaceutically acceptable salts thereof; processes for the preparation thereof; and pharmaceutical compositions comprising these compounds or salts.

14 Claims, No Drawings

TETRAHYDROPYRIDINE DERIVATIVES ACTING ON MUSCARINIC ACETYLCHOLINE RECEPTORS

FIELD OF THE INVENTION

The present invention relates to novel tetrahydropyridine derivatives having substituted pyrrolidinone and oxime, which act on muscarinic acetylcholine receptors and thus useful as nootropics and therapeutic agents for neural diseases; and pharmaceutically acceptable salts thereof; processes for the preparation thereof; and pharmaceutical compositions comprising these compounds or salts.

BACKGROUND OF THE INVENTION

Due to the increase in the number of the elderly population, the number of geriatric diseases such as dementia have increased dramatically. Senile dementia, as represented by Alzheimer's disease, is a degenerative neural disease characterized by disorders of mental capacity including loss of memory, judgment and cognitive function. Patients suffering from Alzheimer's disease show up to 90% degeneration of pre-synapse muscarinic acetylcholine neurons of the basal ganglia, which project into the frontal lobe and hippocampus, both of which manage learning, association, consolidation, and cognitive function such as perception in the cerebrum. However, the post-synapse muscarinic neurons in the forebrain and hippocampus are relatively unchanged. These facts suggest the strategy of medicinal development based on cholinergic deficiency hypothesis, which focuses on the stimulation of post-synapse receptors [See; R. T. Bartus, et al. Science, 217, 408–417 (1982)].

Tacrine is an acetylcholine esterase inhibitor that enhances available acetylcholine, which was developed as an agent involved in cognitive function. However, Tacrine had adverse effects. Recently, Aricept (donepezil, Eisai America, Inc., 1996), Exelon (rivastigmine, Novartis Pharmaceuticals Corporation, 2000) and Reminyl (galantamine hydrobromide, Janssen Research, 2001) having enhanced efficacy were developed [See; W. Greenlee, et al. I1 Farmaco, 2001, 56, 247–250]. However, oxotremorine, RS-86 and the like, which is a nonselective cholinergic agonist for directly stimulating cholinergic receptors, had adverse effects [See; R. Plate et al., Bioorg. Med. Chem., 2000, 8, 449–454].

Muscarinic choline receptors exist in the central and peripheral nervous systems in five subtype forms to play an important role in brain cognitive function. As the post-synapse muscarinic neurons in the forebrain and hippocampus are known to be relatively unchanged in patients suffering from Alzheimer's disease, research in nootropics and therapeutic agents for Alzheimer's disease, focus on developing muscarinic agonists selective for the central nervous system and M1 receptors to decrease adverse effects and increase the efficacy of a cholinergic drug.

Known muscarinic agonists active on the central nervous system include Talsaclidin (1997), YM-796 (1990), CI-1017 (2000), Xanomelin (1997), Milameline (1997), Sabcomeline (SB-202026, 1997), Alvameline (LU 25–109, 1997), AF-102 (1997), etc. [See; A. Fisher, Drug Dev. Res. 2000, 50, 291–297]. Additionally, drugs with pyrrolidine rings and active on the nervous system include agents to ameliorate conditions of Alzheimer's disease such as oxotremorine compound [See; E. J. Trybulski et al., Bioorg. Med. Chem. Lett. 1992, 2, 827–832] and nootropics [See; D. Manetti et al., J. Med. Chem. 2000, 43, 1969–1974]. Although oxadiazole compounds of high affinity and excellent efficacy have been reported, they are known to have adverse effects. Recently, muscarinic agonists such as Pilocarpine (Salagen Tablets, MGI Pharma, Inc., 1998) and Cevimeline (AF102B, EVOXAC™, SnowBrand Pharmaceuticals, Inc., 2000) were approved by FDA as therapeutic agents for xerostomia originating from studies on the Sjogren's syndrome, a variety of autoimmune diseases affecting exocrine glands [See; Drugs of the future, 2000, 25(6), 558–562].

Muscarinic receptors are involved in psychosis, Alzheimer's disease and Parkinson's disease. Compounds that have activity on muscarinic acetylcholine receptors are useful for treatment of pain, glaucoma, schizophrenia, anxiety, manic-depressive psychosis (circular insanity), bipolar psychosis, depression, somnipathy, epilepsy, cerebral ischemia, fecal incontinence, gastrointestinal mobility and gastric secretion disorder [See; L. M. Merritt et al., U.S. Pat. No. 5,998,404].

Recently, the muscarinic receptor in post- and pre-synapse of the cholinergic nervous system, which is known to play an important role in learning and memory, was also found to regulate the process of forming amyloid precursor protein, which plays some role in precipitating beta-amyloid in patients suffering from Alzheimer's disease. Further, muscarinic receptor agonist is known to accelerate secretion of soluble amyloid precursor protein and decrease phosphorylation of tau-protein. Accordingly, to develop nootropics and therapeutic agents for Alzheimer's disease wherein beta-amyloid plaque and nerve fiber entanglement are accumulated, it is important to develop novel muscarinic receptor agonists with muscarinic acetylcholine receptor activity and high efficacy, low cholinergic adverse effects and selectivity for other receptors [See; C. C. Felder et al., J. Med. Chem. 2000, 43, 23, 4334–4353].

However, some compounds active on the muscarinic acetylcholine receptor have adverse effects such as hypersialosis, tearing and gastropathy. Accordingly, there is a need to develop novel compounds that have muscarinic acetylcholine receptor activity, selectivity for other receptors or subtypes, high efficacy and low cholinergic adverse effects.

SUMMARY OF THE INVENTION

The object of the present invention is to provide novel tetrahydropyridine derivatives having appropriately substituted pyrrolidinone and oxime, which show high efficacy, low cholinergic adverse effects and high affinity for muscarinic acetylcholine receptors; and pharmaceutically acceptable salts thereof; processes for the preparation thereof; and pharmaceutical compositions comprising these compounds or salts.

DETAILED DESCRIPTION OF THE PRESENT INVENTION

The present invention provides tetrahydropyridine derivatives of formula 1,

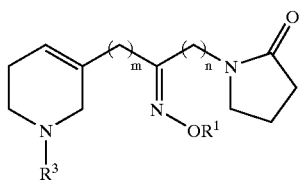

wherein m is 0 or 1, n is 1 or 2, $R^1$ is hydrogen, $C_{1-4}$ alkyl, $C_{2-4}$ alkynyl or aryl, and $R^3$ is $C_{1-4}$ alkyl; and pharmaceutically acceptable salts thereof.

$C_{1-4}$ alkyl as used herein represents a straight or branched alkyl group comprising 1 to 4 carbon atoms, such as ethyl, n-propyl, isopropyl, n-butyl, isobutyl, t-butyl, and most preferably methyl.

$C_{2-4}$ alkynyl as used herein represents a straight or branched hydrocarbon group having one triple bond and comprising 2 to 4 carbon atoms, such as ethynyl, propynyl (generally known as propargyl) butynyl, and most preferably propargyl.

Aryl as used herein represents phenyl, naphthyl or benzyl, and most preferably benzyl.

Most preferable are compounds of formula 1 according to the present invention wherein $R^1$ is hydrogen, methyl, propargyl or benzyl and $R^3$ is methyl.

Preferable compounds of formula 1 are

1-[3-benzyloxyimino-3-(1-methyl-1,2,5,6-tetrahydro-pyridin-3-yl)-propyl]-pyrrolidin-2-one, 1-[2-benzyloxyimino-3-(1-methyl-1,2,5,6-tetrahydro-pyridin-3-yl)-propyl]-pyrrolidin-2-one, 1-[3-methoxyimino-3-(1-methyl-1,2,5,6-tetrahydro-pyridin-3-yl)-propyl]-pyrrolidin-2-one, 1-[2-methoxyimino-3-(1-methyl-1,2,5,6-tetrahydro-pyridin-3-yl)-propyl]-pyrrolidin-2-one, 1-[3-hydroxyimino-3-(1-methyl-1,2,5,6-tetrahydro-pyridin-3-yl)-propyl]-pyrrolidin-2-one, 1-[2-hydroxyimino-3-(1-methyl-1,2,5,6-tetrahydro-pyridin-3-yl)-propyl]-pyrrolidin-2-one, 1-[3-(1-methyl-1,2,5,6-tetrahydro-pyridin-3-yl)-3-propyn-2-yloxyimino-propyl]-pyrrolidin-2-one, 1-[3-(1-methyl-1,2,5,6-tetrahydro-pyridin-3-yl)-2-propyn-2-yloxyimino-propyl]-pyrrolidin-2-one, 1-[2-hydroxyimino-2-(1-methyl-1,2,5,6-tetrahydro-pyridin-3-yl)-ethyl]-pyrrolidin-2-one, 1-[2-methoxyimino-2-(1-methyl-1,2,5,6-tetrahydro-pyridin-3-yl)-ethyl]-pyrrolidin-2-one, 1-[2-(1-methyl-1,2,5,6-tetrahydro-pyridin-3-yl)-2-propyn-2-yloxyimino-ethyl]-pyrrolidin-2-one, 1-[2-benzyloxyimino-2-(1-methyl-1,2,5,6-tetrahydro-pyridin-3-yl)-ethyl]-pyrrolidin-2-one, and pharmaceutically acceptable salts thereof.

Pharmaceutically acceptable salts of compounds of formula 1 include acid addition salts. Acids for making pharmaceutically acceptable acid addition salts include hydrochloric acid, hydrobromic acid, sulfuric acid, phosphoric acid, acetic acid, benzoic acid, sulfonic acid, fumaric acid, maleic acid, citric acid, lactic acid, tartaric acid, oxalic acid, or pharmaceutically acceptable organic and inorganic acid, and the like.

The present invention also provides a process for the preparation of tetrahydropyridine derivatives of formula 1,

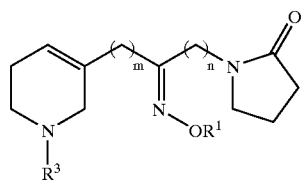

wherein m, n, $R^1$ and $R^3$ are as defined in the above, comprising:

i) performing a condensation reaction of a compound of formula 5,

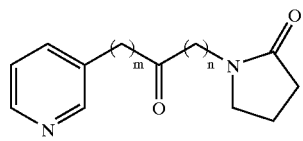

wherein m and n are as defined in the above, with $R^1ONH_2 \cdot HCl$, wherein $R^1$ is as defined in the above, to obtain a compound of formula 8,

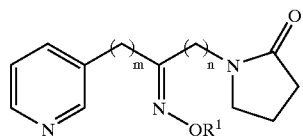

wherein m, n and $R^1$ are as defined in the above; and ii) reacting the resulting compound of formula 8 with an alkyl iodide to form an alkyl pyridine salt, and then reducing the salt to obtain the compound of formula 1.

Below, a process for preparation of tetrahydropyridine derivatives of formula 1 of the present invention will be explained in more detail referring to Schemes 1 and 2.

Scheme 1

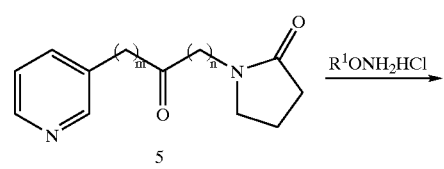

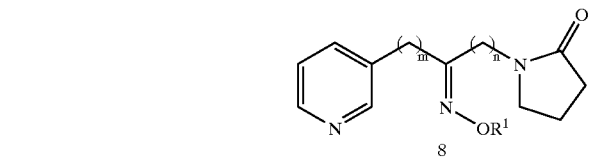

Scheme 2

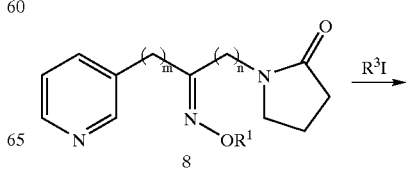

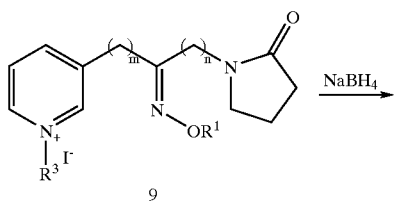

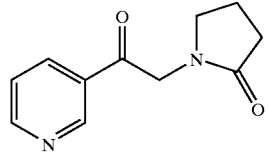

First, the compound of formula 5 is reacted with R¹ONH₂·HCl, such as benzyloxyamine hydrochloride salt, hydroxylamine hydrochloride salt, methyloxyamine hydrochloride salt and propargyloxyamine hydrochloride salt, in methanol/water(1.5:1) for about 12 hours. Subsequently, the reaction product is purified by separation with silica gel column chromatography to obtain the compound of formula 8.

The obtained compound of formula 8 is dissolved in acetone, and reacted with alkyl iodide for 4 hours at 0° C. A small amount of diethyl ether is added and the mixture is filtered. After washing with acetone/diethyl ether and filtrating and drying, the pyridinium iodide salt of formula 9 is obtained. The salt compound is dissolved in ethanol/water (1:1), and reacted with sodium borohydride for 2 hours. Subsequently, the resulting product is purified by separation with silica gel column chromatography to obtain the compound of formula 1.

A compound of formula 5a, which is the compound of formula 5 wherein m is 0 and n is 1, can be synthesized in two ways as follows.

Scheme 3

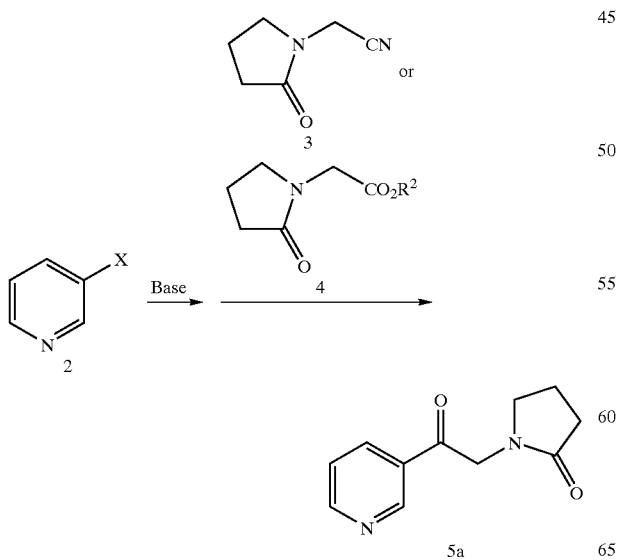

First, as shown in Scheme 3, the compound of formula 5a

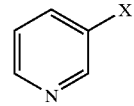

can be obtained by alkylation of halogen at 3-position of a pyridine of formula 2, wherein X is iodine, bromine or chlorine, followed by a reaction with 2-(oxo-pyrrolidin-1-yl)-acetonitrile or 2-(oxo-pyrrolidin-1-yl)-acetic acid ethyl ester.

More specifically, after fully dissolving the compound of formula 2 in diethyl ether with stirring, a base such as n-butyl lithium is added dropwise for 30 minutes at −78° C. After reacting for 30 minutes, 2-(oxo-pyrrolidin-1-yl)-acetonitrile or 2-(oxo-pyrrolidin-1-yl)-acetic acid ethyl ester are added dropwise for 30 minutes at −78° C. After slowly increasing to room temperature, the reaction is preceded at room temperature for about 6 hours. Subsequently, the resulting product is purified by separation with silica gel column chromatography to obtain the compound of formula 5a.

Scheme 4

Second, as shown in Scheme 4, the compound of formula 5a can be synthesized by the coupling reaction of the compound of formula 2a wherein X' is B(OR)₂, B⁻(OR)₃Li⁺ or SnBu₃ and R is hydrogen or C₁₋₄ alkyl, with 1-(2-bromoallyl)-pyrrolidin-2-one, followed by an ozonolysis.

More specifically, tributyltin, dimethylborate, or trimethylborate lithium salt of 3-pyridyl compound of formula 2a together with the solution of ditriphenylphosphine palladium dichloride and sodium carbonate are added to the solution of 1-(2-bromoallyl)-pyrrolidin-2-one, and the mixture is reacted for 15 minutes at room temperature and then heated at reflux for 18 hours. Subsequently, the resulting product is purified by separation with silica gel column chromatography to obtain the compound of formula 5a.

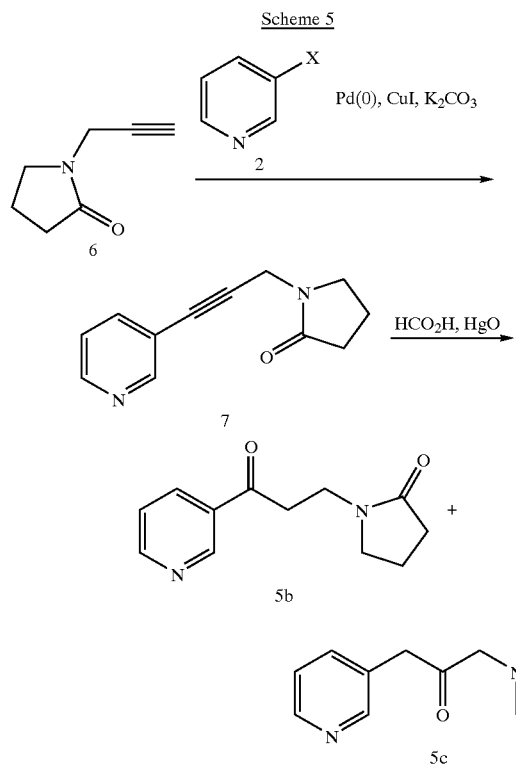

Further, as shown in Scheme 5, the compounds of formula 5b and 5c, which are the compounds of formula 5 wherein m=0 and n=2, and m=1 and n=1, respectively,

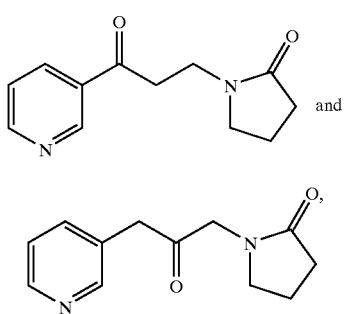

can be prepared by performing a coupling reaction with the compound of formula 6

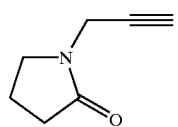

and the compound of formula 2, to obtain the alkyne compound of formula 7

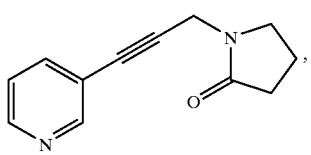

and then performing a hydration reaction to the alkyne compound of formula 7.

More specifically, the compound of formula 6 is reacted with the compound of formula 2 in dimethoxyethane/water (1:1) in the presence of a catalyst of tetrakis triphenylphosphine palladium, copper iodide and potassium carbonate to obtain the compound of formula 7. After isolating this compound of formula 7 and reacting with formic acid and mercury oxide, the resulting product is purified by separation with silica gel column chromatography. The former separated material is the compound of formula 5b while the latter one is the compound of formula 5c.

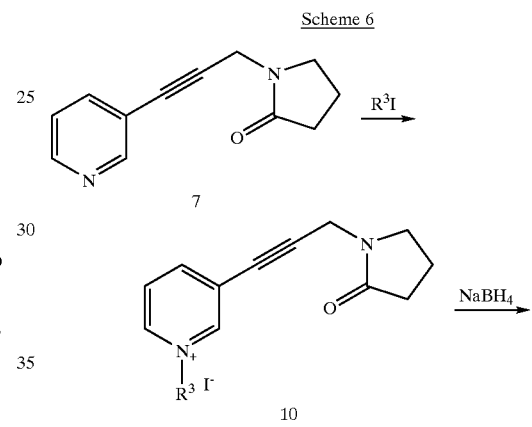

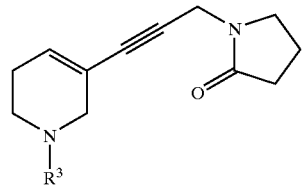

Additionally, as shown in Scheme 6, the tetrahydropyridine compound of formula 11 can be prepared from the pyridine compound of formula 7 by the same preparation method as for the compound of formula 1.

Preferable compounds of formula 5 are 1-(3-oxo-3-pyridin-3-yl-propyl)-pyrrolidin-2-one, 1-(2-oxo-3-pyridin-3-yl-propyl)-pyrrolidin-2-one and 1-(2-oxo-2-pyridin-3-yl-ethyl)-pyrrolidin-2-one.

Preferable compounds of formula 8 are
  1-(3-benzyloxyimino-3-pyridin-3-yl-propyl)-pyrrolidin-2-one,
  1-(2-benzyloxyimino-3-pyridin-3-yl-propyl)-pyrrolidin-2-one,
  1-(3-methoxyimino-3-pyridin-3-yl-propyl)-pyrrolidin-2-one,
  1-(2-methoxyimino-3-pyridin-3-yl-propyl)-pyrrolidin-2-one,
  1-(3-hydroxyimino-3-pyridin-3-yl-propyl)-pyrrolidin-2-one,
  1-(2-hydroxyimino-3-pyridin-3-yl-propyl)-pyrrolidin-2-one, 1-(3-propyn-2-yloxyimino-3-pyridin-3-yl-propyl)-pyrrolidin-2-one, 1-(2-propyn-2-yloxyimino-3-pyridin-3-yl-propyl)-pyrrolidin-2-one, 1-(2-hydroxyimino-2-pyridin-3-yl-ethyl)-pyrrolidin-2-one, 1-(2-methoxyimino-2-pyridin-3-yl-ethyl)-pyrrolidin-2-one, 1-(2-propyn-2-yloxyimino-2-pyridin-3-yl-ethyl)-pyrrolidin-2-one, 1-(2-benzyloxyimino-2-pyridin-3-yl-ethyl)-pyrrolidin-2-one, and pharmaceutically acceptable salts thereof.

Preferable compounds of formula 11 are 1-[3-(1-methyl-1,2,5,6-tetrahydro-pyridin-3-yl)-propyn-2-yl]-pyrrolidin-2-one and pharmaceutically acceptable salts thereof.

Free forms of compounds of formula 1 can be converted into acid addition salts by conventional methods such as addition of a solution containing appropriate acid in stoichiometric amounts. Pharmaceutically acceptable acids include hydrochloric acid, hydrobromic acid, sulfuric acid, phosphoric acid, acetic acid, benzoic acid, sulfonic acid, fumaric acid, maleic acid, citric acid, lactic acid, tartaric acid, oxalic acid, or pharmaceutically acceptable organic and inorganic acid, and the like.

Additionally, the present invention provides a pharmaceutical composition comprising a compound of formula 1 or a pharmaceutically acceptable salt thereof as an active ingredient together with a conventional carrier.

The compound of the present invention active on muscarinic acetylcholine receptor is useful for treating psychosis, Alzheimer's disease, Parkinson's disease, and the like. Further, they are useful for pain, glaucoma, schizophrenia, anxiety, manic-depressive psychosis (circular insanity), bipolar psychosis, depression, somnipathy, epilepsy, cerebral ischemia, sjogren's syndrome, fecal incontinence, gastrointestinal mobility and gastric secretion disorder.

The pharmaceutical composition of the present invention can be administered orally or parenterally, such as intravenously or intramuscularly, in conventional manner.

The dosage depends on age, condition and weight of a patient, and the route of administration. The dosage amount of an active ingredient is typically about 0.01 to 200 mg per kg of body weight per day.

The compound of the present invention may be used as conventional solids or liquid formulations, for example in the form of non-coating or thin film-coating tablets, capsules, powders, granules or solutions. They are prepared with conventional methods, and active ingredient may be processed together with conventional pharmaceutical adjuvant, such as tablet binder, extender, preservative, tablet disintegrant, fluidity controller, plasticizer, wetting agent, dispensing agent, emulsifier, solvent, sustained releasing agent and/or antioxidant.

The following examples illustrate the invention in detail but one skilled in the art will appreciate that they are not intended to limit the scope of the invention.

EXAMPLES

EXAMPLE 1

Preparation of 1-(3-pyridin-3-yl-propyn-2-yl)-pyrrolidin-2-one

After dissolving 50.0 g (0.59 mol) of 2-pyrrolidinone in 300 mL of methanol/tetrahydropuran (1:2), 66.0 g (0.59 mol) of potassium t-butoxide was added, and the mixture was stirred for 12 hours at room temperature. Once the reaction was completed, the reaction mixture was concentrated under reduced pressure. After adding toluene, the mixture was concentrated under reduced pressure about two or three times more in order to remove solvent sufficiently. The mixture was then washed with toluene and filtered to obtain 65.5 g (90% yield) of pyrrolidinone potassium salt. 15 g (0.12 mol) of this compound was then added to toluene and acetonitrile separately, and 17.40 g (0.15 mol) of propargyl bromide was added dropwise for one hour and the mixture was reacted at room temperature. As propargyl bromide was added dropwise, heat got emitted. For this reasons, the reactor was cooled in a water bath. When reacted in toluene, the mixture was reacted at 45 to 50° C. after completing the dropwise addition. Upon completion of the reaction, the reaction mixture was concentrated under reduced pressure and the product was purified by separation with silica gel column chromatography using ethyl acetate/n-hexane (1:1), to obtain 8.30 g (45% yield, toluene solvent) and 13.85 g (75% yield, acetonitrile solvent) each of 1-propyn-2-yl-pyrrolidin-2-one. After adding 15.0 g (0.12 mol) of 1-propyn-2-yl-pyrolridin-2-one and 28.0 g (0.18 mol) of 3-bromopyridine to 300 mL of dimethoxyethane/water (1:1), 2 mol% of tetrakis triphenyl phosphpine palladium and 4% of copper iodide, and 2.5 equiv. of potassium carbonate were added, thereafter, the mixture was reacted for 12 hours at 80° C. Upon completion of the reaction, the reaction mixture was filtered through cellite, extracted with ethyl acetate, and dried over anhydrous sodium sulfate. The product was purified by separation with silica gel column chromatography (ethyl acetate followed by chloroform/methanol (20:1)), to obtain 16.82 g (70% yield) of 1-(3-pyridin-3-yl-propyn-2-yl)-pyrrolidin-2-one.

$^1$H NMR(CDCl$_3$): δ8.65–7.23 (m, 4H), 4.35 (s, 2H), 3.55 (t, J=7.11, 2H), 2.42 (t, J=7.98, 2H), 2.14–2.03 (m, 2H); MS (m/e): 200 (M$^+$), 172, 144, 116, 89, 63.

EXAMPLE 2

Preparation of 1-(3-oxo-3-pyridin-3-yl-propyl)-pyrrolidin-2-one 10.0 g (0.05 mol) of 1-(3-pyridin-3-yl-propyn-2-yl)-pyrrolidin-2-one prepared from Example 1 was added to 150 mL of formic acid, and 10.8 g of mercury oxide was added, and then the mixture was reacted for 12 hours at 100~110° C. Upon completion of the reaction, the reaction mixture was concentrated under reduced pressure, and extracted with chloroform/saturated sodium biscarbonate solution for three times, and dried over anhydrous sodium sulfate. Two structural isomers were resulted from the reaction, and purified by separation with silica gel column chromatography (chloroform/methanol (40:1)) to obtain 4.14 g (38% yield) of 1-(3-oxo-3-pyridin-3-yl-propyl)-pyrrolidin-2-one, which firstly seperated out.

$^1$H NMR (CDCl$_3$): δ9.13–7.38 (m, 4H), 3.68 (t, J=1.27, 2H), 3.47 (t, J=7.08, 2H), 3.27 (t, J=8.28, 2H), 2.33 (t, J=8.28, 2H), 2.04–1.94 (m, 2H); MS (m/e): 218 (M$^+$), 190, 133, 112, 98, 78, 51.

EXAMPLE 3

Preparation of 1-(2-oxo-3-pyridin-3-yl-propyl)-pyrrolidin-2-one

The procedure was carried out as described in Example 2, and purified by separation with silica gel column chromatography using chloroform/methanol (40:1) to obtain 2.29 g (21% yield) of 1-(2-oxo-3-pyridin-3-yl-propyl)-pyrrolidin-2-one, which lately separated out.

$^1$H NMR (CDCl$_3$): δ8.55–7.27 (m, 4H), 4.20 (s, 2H), 3.77 (s, 2H), 3.41 (t, J=7.04, 2H), 2.43 (t, J=8.23, 2H), 2.12–2.02 (m, 2H); MS (m/e): 218 (M$^+$), 190, 126, 120, 98, 70.

EXAMPLE 4
Preparation of 1-(3-benzyloxyimino-3-pyridin-3-yl-propyl)-pyrrolidin-2-one 1.10 g (6.87 mmol) of benzyloxyamine hydrochloride salt and 0.36 g of sodium were added to 1.0 g (4.58 mmol) of 1-(3-oxo-3-pyridin-3-yl-propyl)-pyrrolidin-2-one prepared from Example 2 in methanol/water (1.5:1), and the mixture was reacted for 12 hours at 0° C. Upon completion of the reaction, the reaction mixture was concentrated under reduced pressure, and extracted with ethyl acetate. After concentrating again, the reaction mixture was purified by separation with silica gel column chromatography using chloroform/methanol (20:1) to obtain 1.04 g (70% yield) of 1-(3-benzyloxyimino-3-pyridin-3-yl)-pyrrolidin-2-one as E/Z mixture (3.1:1).

$^1$H NMR(CDCl$_3$): δ8.91–7.29 (m, 9H), 5.25, 5.07 (2s, 1H), 3.51–3.44 (m, 2H), 3.25–3.20 (m, 2H), 3.01,2.75 (2t, J=7.02, 2H), 2.21–2.16 (m, 2H), 1.80–1.71 (m, 2H); MS (m/e): 323 (M$^+$), 238, 216, 91, 70.

EXAMPLE 5
Preparation of 1-(2-benzyloxyimino-3-pyridin-3-yl-propyl-pyrrolidin-2-one Using the method of Example 4, 0.92 g (62% yield) of 1-(2-benzyloxyimino-3-pyridin-3-yl-propyl-pyrrolidin-2-one was prepared as E/Z mixture (1.1:1) from 1 g (4.58 mmol) of 1-(2-oxo-3-pyridin-3-yl-propyl)-pyrrolidin-2-one prepared from Example 3 and 1.10 g (6.87 mmol) of benzyloxyamine hydrochloride salt.

$^1$H NMR(CDCl$_3$): δ8.50–7.16 (m, 9H), 5.16, 5.13 (2s, 1H), 4.15, 3.98 (2s, 2H), 3.65, 3.09 (2s, 2H), 3.04, 2.97 (2t, J=7.09, 2H), 2.26–2.17 (m, 2H), 1.73–1.27 (m, 2H); MS (m/e): 323 (M$^+$), 238, 216, 183, 91.

EXAMPLE 6
Preparation of 1-(3-methoxyimino-3-pyridin-3-yl-propyl)-pyrrolidin-2-one Using the method of Example 4, 1.05 g (93% yield) of 1-(3-methoxyimino-3-pyridin-3-yl-propyl)-pyrrolidin-2-one was prepared as E/Z mixture (3.7:1) from 1.0 g (4.58 mmol) of 1-(3-oxo-3-pyridin-3-yl-propyl)-pyrrolidin-2-one prepared from Example 2 and 0.57 g (6.87 mmol) of methyloxyamine hydrochloride salt.

$^1$H NMR(CDCl$_3$): δ8.91–7.30 (m, 4H), 4.03, 3.84 (2s, 2H), 3.53–3.47 (m, 2H), 3.43–3.36 (m, 2H), 2.99, 2.78 (2t, J=7.23, 2H), 2.31–2.28 (m, 2H), 1.96–1.87 (m, 2H); MS (m/e): 247 (M$^+$), 216, 131, 98, 70.

EXAMPLE 7
Preparation of 1-(2-methoxyimino-3-pyridin-3-yl-propyl)-pyrrolidin-2-one Using the method of Example 4, 1.05 g (93% yield) of 1-(2-methoxyimino-3-pyridin-3-yl-propyl)-pyrrolidin-2-one was prepared as E/Z mixture (1.3:1) from 1.0 g (4.58 mmol) of 1-(2-oxo-3-pyridin-3-yl-propyl)-pyrrolidin-2-one prepared from Example 3 and 0.57 g (6.87 mmol) of methyloxyamine hydrochloride salt.

$^1$H NMR(CDCl$_3$): δ8.44–7.13 (m, 4H), 4.06, 3.93 (2s, 2H), 3.87, 3.83 (2s, 3H), 3.56, 3.42 (2s, 2H), 3.03, 2.96 (2t, J=9, 2H), 2.21–2.15 (m, 2H), 2.15–1.60 (m, 1H); MS (m/e): 247 (M$^+$), 216, 164, 131, 98, 70.

EXAMPLE 8
Preparation of 1-(3-hydroxyimino-3-pyridin-3-yl-propyl)-pyrrolidin-2-one Using the method of Example 4, 0.59 g (55% yield) of 1-(3-hydroxyimino-3-pyridin-3-yl-propyl)-pyrrolidin-2-one was prepared as E/Z mixture (8.24:1) from 1.0 g (4.58 mmol) of 1-(3-oxo-3-pyridin-3-yl-propyl)-pyrrolidin-2-one prepared from Example 2 and 0.48 g (6.87 mmol) of hydroxylamine hydrochloride salt.

$^1$H NMR(CDCl$_3$): δ11.76, 11.23 (2s, 1H), 8.99–7.28 (m, 4H), 3.61–3.55 (m, 2H), 3.46–3.40 (m, 2H), 3.09–3.05 (m, 2H), 2.35–2.30 (m, 2H), 1.95–1.85 (m, 2H); $^{13}$C NMR (CDCl$_3$): major isomer δ175.97, 153.58, 149.54, 147.45, 134.38, 132.54, 123.94, 48.22, 39.88, 31.30, 24.50, 18.36; minor isomer δ175.96, 151.50, 149.63, 149.05, 136.95, 129.94, 123.71, 47.83, 40.59, 32.98, 31.32, 18.27; MS (m/e): 233 (M$^+$), 216, 148, 98.

EXAMPLE 9
Preparation of 1-(2-hydroxyimino-3-pyridin-3-yl-propyl)-pyrrolidin-2-one Using the method of Example 4, 0.93 g (87% yield) of 1-(-2-hydroxyimino-3-pyridin-3-yl-propyl)-pyrrolidin-2-one was prepared as E/Z mixture (1.55:1) from 1.0 g (4.58 mmol) of 1-(2-oxo-3-pyridin-3-yl-propyl)-pyrrolidin-2-one prepared from Example 3 and 0.48 g (6.87 mmol) of hydroxylamine hydrochloride salt.

$^1$H NMR(CDCl$_3$): δ11.86, 11.75 (2s, 1H), 8.63–7.25 (m, 4H), 4.26, 4.05 (2s, 2H), 3.73, 3.54 (2s, 2H), 3.20–3.11(m, 2H), 2.32–2.25 (m, 2H), 1.81–1.66 (m, 2H); $^{13}$C NMR (CDCl$_3$): major isomer δ176.03, 153.12, 150.16, 147.84, 137.71, 133.35, 123.99, 47.16, 45.98, 31.51, 31.04, 29.93, 17.74; minor isomer δ176.22, 153.66, 150.03, 147.60, 137.53, 133.48, 123.89, 48.43, 38.51, 36.35, 30.73, 17.92; MS (m/e): 173 (M$^+$), 233, 216, 148, 98.

EXAMPLE 10
Preparation of 1-(3-propyn-2-yloxyimino-3-pyridin-3-yl-propyl)-pyrrolidin-2-one Using the method of Example 4, 0.98 g (79% yield) of 1-(3-propyn-2-yloxyimino-3-pyridin-3-yl-propyl)-pyrrolidin-2-one was prepared as E/Z mixture (2.72:1) from 1.0 g (4.58 mmol) of 1-(3-oxo-3-pyridin-3-yl-propyl)-pyrrolidin-2-one prepared from Example 2 and 0.74 g (6.87 mmol) of propargyloxyamine hydrochloride salt.

$^1$H NMR(CDCl$_3$): δ8.93–7.31(m, 4H), 4.83, 4.64 (2d, J=2.34, 2H), 3.56–63.51 (m, 2H), 3.44–3.40 (m, 2H), 3.03, 2.82 (2t, J=7.05, 2H), 2.53, 2.48 (2t, J=2.28, 2H), 2.35–2.26 (m, 2H), 2.00–1.86 (m, 2H); $^{13}$C NMR(CDCl$_3$): major isomer δ175.47, 155.67, 150.71, 147.87, 131.18, 123.79, 79.80, 75.22, 62.49, 48.06, 39.95, 31.10, 25.38, 18.31; minor isomer δ175.39, 154.10, 150.35, 148.99, 136.49, 129.87, 123.51, 80.13, 74.87, 61.99, 47.62, 40.06, 33.23, 31.25, 18.36; MS (m/e): 271(M$^+$), 228, 186, 173, 144, 131, 98.

EXAMPLE 11
Preparation of 1-(2-propyn-2-yloxyimino-3-pyridin-3-yl-propyl)-pyrrolidin-2-one Using the method of Example 4, 0.92 g (74% yield) of 1-(2-propyn-2-yloxyimino-3-pyridin-3-yl-propyl)-pyrrolidin-2-one was prepared as E/Z mixture (1.04:1) from 1.0 g (4.58 mmol) of 1-(2-oxo-3-pyridin-3-yl-propyl)-pyrrolidin-2-one prepared from Example 3 and 0.74 g (6.87 mmol) of propargyloxyamine hydrochloride salt.

$^1$H NMR(CDCl$_3$): δ8.54–7.22 (m, 4H), 4.75, 4.72 (2d, J=2.34, 2H), 4.15, 4.07 (2s, 2H), 3.67, 3.53 (2s, 2H), 3.17–3.06 (m, 2H), 2.57–2.55 (m, 1H), 2.28–2.23 (m, 2H), 1.78–1.71 (m, 2H); $^{13}$C NMR(CDCl$_3$): major isomer δ175.59, 155.17, 150.47, 148.39, 136.81, 131.90, 123.74, 79.75, 75.24, 61.92, 48.12, 39.10, 30.63, 30.46, 17.77; minor isomer δ175.72, 156.04, 150.36, 148.66, 136.66, 132.21, 123.64, 79.84, 75.12, 61.89, 46.92, 45.49, 36.22, 30.84, 17.88; MS (m/e): 271 (M$^+$), 253, 169, 147, 98.

EXAMPLE 12
Preparation of 1-[3-benzyloxyimino-3-(1-methyl-1,2,5,6-tetrahydro-pyridin-3-yl)-propyl]-pyrrolidin-2-one 0.5 g (1.55 mmol) of 1-(3-benzyloxyimino-3-pyridin-3-yl-propyl)-pyrrolidin-2-one prepared from Example 4 was dissolved in 1mL of acetone, and then 0.66 g (4.65 mmol) of methyl iodide was added. The mixture was reacted for 4 hours at 0° C. A small amount of diethyl ether was added and the mixture was filtered. The filtrate was washed with acetone/diethyl ether, filtered again and dried to obtain pyridine iodide salt. After 0.5 g of this salt compound was dissolved in ethanol/water (1:1), 3.0 equiv. of sodium borohydride was added and reacted for 2 hours. Upon completion of the reaction, the reaction mixture was concentrated under reduced pressure, extracted with chloroform for 3 times, washed with brine and water, dried over sodium sulfate, and concentrated under reduced pressure. The concentrated compound was purified by separation with silica gel column chromatography using chloroform/methanol (20:1~10:1) to obtain 0.48 g (91% yield) of 1-[3-benzyloxyimino-3-(1-methyl-1,2,5,6-tetrahydro-pyridin-3-yl)-propyl]-pyrrolidin-2-one as E/Z mixture (9.86:1).

$^1$H NMR(CDCl$_3$): δ7.36–7.27 (m, 5H), 6.26, 5.98 (2t, J=3.69, 1H), 5.12, 5.04 (2s, 2H), 3.45–3.36 (m, 2H), 3.34–3.17 (m, 4H), 2.74 (t, J=7.17, 2H), 2.50–2.48 (m, 2H), 2.40–2.25 (m, 7H), 1.91–1.88 (m, 2H); $^{13}$C NMR(CDCl$_3$): δ175.28, 155.90, 138.31, 133.01, 128.73, 128.61, 128.33, 128.22, 76.64, 53.99, 51.88, 48.20, 46.34, 40.49, 31.30, 27.26, 23.36, 18.44; MS (m/e): 341 (M$^+$), 234, 149, 121, 91.

EXAMPLE 13
Preparation of 1-[2-benzyloxyimino-3-(1-methyl-1,2,5,6-tetrahydro-pyridin-3-yl)-propyl]-pyrrolidin-2-one 0.5 g (1.55 mmol) of 1-(2-benzyloxyimino-3-pyridin-3-yl-propyl-pyrrolidin-2-one prepared from Example 5 was treated as described in Example 12 to obtain 0.48 g (63% yield) of 1-[2-benzyloxyimino-3-(1-methyl-1,2,5,6-tetrahydro-pyridin-3-yl)-propyl]-pyrrolidin-2-one as E/Z mixture (1.01:1).

$^1$H NMR(CDCl$_3$): δ7.34–7.28 (m, 5H), 5.59, 5.53 (2s, 1H), 5.09, 5.08 (2s, 2H), 4.14, 3.93 (2s, 2H), 3.41–3.21(m, 2H), 2.96, 2.80 (2s, 2H), 2.75–2.73 (m, 2H), 2.42–2.17 (m, 7H), 1.97–1.96 (m, 2H), 1.65–1.60 (m, 2H); $^{13}$C NMR (CDCl$_3$): major isomer δ175.31, 153.98, 138.19, 131.35, 128.74, 128.63, 128.25, 122.48, 76.29, 57.75, 52.01, 47.27, 46.18, 46.12, 45.15, 38.60, 32.92, 26.55, 18.21; minor isomer δ175.47, 154.80, 138.11, 130.62, 128.67, 128.55, 128.19, 123.02, 76.33, 57.13, 51.90, 48.39, 38.93, 31.19 30.81, 26.90, 18.14; MS (m/e): 341 (M$^+$), 234, 149, 121, 91, 78.

EXAMPLE 14
Preparation of 1-[3-methoxyimino-3-(1-methyl-1,2,5,6-tetrahydro-pyridin-3-yl)-propyl]-pyrrolidin-2-one 0.5 g (2.02 mmol) of 1-(3-methoxyimino-3-pyridin-3-yl-propyl)-pyrrolidin-2-one prepared from Example 6 was treated as described in Example 12 to obtain 0.34 g (63% yield) of 1-[3-methoxyimino-3-(1-methyl-1,2,5,6-tetrahydro-pyridin-3-yl)-propyl]-pyrrolidin-2-one as E/Z mixture (5.08:1).

$^1$H NMR(CDCl$_3$): δ6.27, 5.01 (2s, 1H), 3.88 (s, 3H), 3.43–3.36 (m, 4H), 3.19 (s, 2H), 2.74–2.68 (m, 2H), 2.53–2.31 (m, 9H), 2.31–1.94 (m, 2H); MS (m/e): 265 (M$^+$), 234, 149, 121, 94, 70.

EXAMPLE 15
Preparation of 1-[2-methoxyimino-3-(1-methyl-1,2,5,6-tetrahydro-pyridin-3-yl)-propyl]-pyrrolidin-2-one 0.5 g (2.02 mmol) of 1-(2-methoxyimino-3-pyridin-3-yl-propyl)-pyrrolidin-2-one prepared from Example 7 was treated as described in Example 12 to obtain 0.49 g (93% yield) of 1-[2-methoxyimino-3-(1-methyl-1,2,5,6-tetrahydro-pyridin-3-yl)-propyl]-pyrrolidin-2-one as E/Z mixture (1.47:1).

$^1$H NMR(CDCl$_3$): δ5.64, 5.56 (2s, 1H), 4.12, 3.95 (2s, 2H), 3.85, 3.84 (2s, 3H), 3.37–3.32 (m, 2H), 2.93(s, 1H), 2.80 (s, 3H), 2.46–2.35 (m, 7H), 2.19 (s, 2H), 2.04–1.98 (m, 2H); $^{13}$C NMR(CDCl$_3$): major isomer δ175.40, 154.13, 131.26, 130.50, 122.27, 61.87, 57.65, 51.86, 47.26, 46.13, 38.36, 31.14, 26.49, 18.08; minor isomer δ175.47, 154.13, 131.26, 122.90, 61.98, 57.15, 51.95, 48.36, 45.13, 38.51, 32.50, 30.79, 18.18; MS (m/e): 265 (M$^+$), 234, 149, 94.

EXAMPLE 16
Preparation of 1-[3-hydroxyimino-3-(1-methyl-1,2,5,6-tetrahydro-pyridin-3-yl)-propyl]-pyrrolidin-2-one 0.5 g (2.14 mmol) of 1-(3-hydroxyimino-3-pyridin-3-yl-propyl)-pyrrolidin-2-one prepared from Example 8 was treated as described in Example 12 to obtain 0.59 g (35% yield) of 1-[3-hydroxyimino-3-(1-methyl-1,2,5,6-tetrahydro-pyridin-3-yl)-propyl]-pyrrolidin-2-one.

$^1$H NMR(CDCl$_3$): δ6.24 (s, 1H), 3.44–3.38 (m, 4H), 3.23 (s, 2H), 2.75 (t, J=7.44, 2H), 2.57 (t, J=5.49, 2H), 2.42–2.34 (m, 7H), 2.01–1.91 (m, 2H); $^{13}$C NMR(CDCl$_3$): δ175.56, 155.23, 132.73, 126.41, 53.67, 51.67, 51.55, 48.33, 45.84, 40.33, 31.42, 30.08, 26.46, 22.48, 18.49; MS (m/e): 251 (M$^+$), 149, 135, 94, 70.

EXAMPLE 17
Preparation of 1-[2-hydroxyimino-3-(1-methyl-1,2,5,6-tetrahydro-pyridin-3-yl)-propyl]-pyrrolidin-2-one 0.5 g (2.14 mmol) of 1-(2-hydroxyimino-3-pyridin-3-yl-propyl)-pyrrolidin-2-one prepared from Example 9 was treated as described in Example 12 to obtain 0.93 g (61% yield) of 1-[2-hydroxyimino-3-(1-methyl-1,2,5,6-tetrahydro-pyridin-3-yl)-propyl]-pyrrolidin-2-one as E/Z mixture (2.95:1).

$^1$H NMR(CDCl$_3$): δ5.63, 5.56 (2m, 1H), 3.44–3.38 (m, 4H), 3.23 (s, 2H), 2.75 (t, J=7.08, 2H), 2.57 (t, J=5.55, 2H), 2.42–2.32 (m, 7H), 2.01–1.91 (m, 2H); $^{13}$C NMR(CDCl$_3$): major isomer δ175.83, 153.19, 130.72, 122.15, 57.38, 51.74, 47.47, 45.87, 45.35, 38.22, 31.27, 26.12, 18.13; minor isomer δ175.70, 153.39, 131.24, 122.80, 56.61, 51.82, 48.44, 45.97, 37.93, 31.94, 31.01, 26.12, 18.23; MS (m/e): 251 (M$^+$), 234, 149, 135, 94, 70.

EXAMPLE 18
Preparation of 1-[3-(1-methyl-1,2,5,6-tetrahydro-pyridin-3-yl)-3-propyn-2-yloxyimino-propyl]-pyrrolidin-2-one 0.5 g (1.84 mmol) of 1-(3-propyn-2-yloxyimino-3-pyridin-3-yl-propyl)-pyrrolidin-2-one prepared from Example 10 was treated as described in Example 12 to obtain 0.98 g (76% yield) of 1-[3-(1-methyl-1,2,5,6-tetrahydro-pyridin-3-yl)-3-propyn-2-yloxyimino-propyl]-pyrrolidin-2-one.

$^1$H NMR(CDCl$_3$): δ6.29, 5.92 (2m, 1H), 4.65, 4.56 (2d, J=2.31, 2H), 3.39–3.35 (m, 4H), 3.14 (m, 2H), 2.73–2.71 (m, 2H), 2.73–2.71 (m, 2H), 2.47–2.28 (m, 10H), 1.98–1.95 (m, 2H); $^{13}$C NMR(CDCl$_3$): δ175.33, 156.86, 132.72, 128.55, 80.20, 74.63, 61.99, 53.86, 51.80, 48.30, 46.29, 40.58, 31.31, 27.26, 23.27, 18.48; MS (m/e): 289 (M$^+$), 273, 175, 161, 70.

EXAMPLE 19
Preparation of 1-[3-(1-methyl-1,2,5,6-tetrahydro-pyridin-3-yl)-2-propyn-2-yloxyimino-propyl]-pyrrolidin-2-one 0.5 g (1.84 mmol) of 1-(2-propyn-2-yloxyimino-3-pyridin-3-yl-propyl)-pyrrolidin-2-one prepared from Example 11 was treated as described in Example 12 to obtain 0.92 g (74% yield) of 1-[3-(1-methyl-1,2,5,6-tetrahydro-pyridin-3-yl)-2-propyn-2-yloxyimino-propyl]-pyrrolidin-2-one as E/Z mixture (1.43:1).

$^1$H NMR(CDCl$_3$): δ5.66, 5.59 (2s, 1H), 4.65 (d, J=2.58, 2H), 4.14, 3.98 (2s, 2H), 3.36 (t, J=6.99, 2H), 2.96–2.84 (m, 4H), 2.50–2.35 (m, 8H), 2.36–2.34 (m, 2H), 2.06–1.96 (m, 2H); $^{13}$C NMR(CDCl$_3$): major isomer δ175.64, 155.15, 130.16, 122.73, 80.16, 74.71, 61.67, 57.51, 51.82, 47.35, 46.03, 38.45, 32.79, 31.19, 26.41, 18.17; minor isomer δ175.70, 155.88, 130.91, 123.28, 80.08, 74.84, 61.74, 57.52, 51.91, 48.41, 46.03, 45.01, 38.74, 30.83, 26.41, 18.26; MS (m/e): 289 (M$^+$), 245, 162, 119.

EXAMPLE 20
Preparation of 1-(2-oxo-2-pyridin-3-yl-ethyl)-pyrrolidin-2-one 5.0 g (31.7 mmol) of 3-bromopyridine was added to 50 mL of diethyl ether. After fully dissolving with stirring, 25 mL of n-butyl lithium (1.6M hexane solution) was added dropwise at −78° C. for 30 minutes. After reacting for 30 minutes, 5.4 g (31.7 mmol) of 2-(oxo-pyrrolidin-1-yl)-acetic acid ethyl ester was added dropwise at −78° C. for 30 minutes.

Thereafter, the reaction was carried out while slowly increasing to room temperature. After reacting for about 6 hours at room temperature, the reaction was checked by TLC and then terminated. The reaction solution was washed with water, the organic layer was separated and the aqueous solution layer was extracted again with ethyl acetate for five times. This extracted layer and the separated organic layer were combined, and dried over sodium sulfate. They were concentrated under reduced pressure, and purified by separation with silica gel column chromatography (chloroform/methanol (30:1)) to obtain 1.22 g (19% yield) of 1-(2-oxo-2-pyridin-3-yl-ethyl)-pyrrolidin-2-one.

$^1$H NMR(CDCl$_3$): δ9.12–7.37 (m, 4H), 4.69 (s, 2H), 3.45 (t, J=6.99, 2H), 2.41 (t, J=7.89, 2H), 2.11–2.01 (m, 2H); $^{13}$C NMR(CDCl$_3$): δ193.39, 176.27, 154.51, 149.71, 135.77, 124.25, 49.57, 48.26, 30.66, 18.43; MS (m/e): 204 (M$^+$), 176, 121, 98, 70.

EXAMPLE 21
Preparation of 1-(2-oxo-2-pyridin-3-yl-ethyl)-pyrrolidin-2-one

To a suspension of 5.0 g (40.6 mmol) of pyrrolidinone potassium salt prepared from Example 1 in 40 mL of toluene, solution of 5.24 mL (2 equiv.) of 2,3-dibromopropene in 10 mL of toluene was added dropwise for 1 hour in water bath and the reaction mixture was reacted at 60~70° C. for 2 hours. Upon completion of the reaction, the mixture was cooled to 0° C. and filtered to remove solid. It was then concentrated under reduced pressure and purified by separation with silica gel column chromatography (ethyl acetate/n-hexane (1:1)) to obtain 5.30 g (64% yield) of 1-(2-bromoallyl)-pyrrolidin-2-one. To degassed solution of 1.0 g (4.90 mmol) of 1-(2-bromoallyl)-pyrrolidin-2-one prepared in the above in 50 mL of ethanol/benzene (1:1), 5 mol% (172 mg) of ditriphenylphosphine palladium dichloride, degassed solution of 7.35 mL of 2N sodium carbonate and 3-pyridyl-tributyltin, dimethyl borate, trimethyl borate lithium salt, boronic acid propanediol ring ester (2 equiv.), etc. were added. The mixture was reacted for 15 minutes at room temperature, followed by heating at reflux for 18 hours. After concentrating under reduced pressure, it was extracted with ethyl acetate for three times and washed with brine for two times. The concentrated solution was purified by separation with silica gel column chromatography (ethyl acetate followed by methylene chloride/methanol (20:1)) to obtain 810 mg (82% yield) of 1-(2-pyridin-3-yl-allyl)-pyrrolidin-2-one. Ozones were added to solution of 100 mg (0.494 mmol) of 1-(2-pyridin-3-yl-allyl)-pyrrolidin-2-one at −78° C. to obtain 1-(2-oxo-2-pyridin-3-yl-ethyl)-pyrrolidin-2-one, which was the same as synthesized in Example 20.

Data for 1-(2-pyridin-3-yl-allyl)-pyrrolidin-2-one; $^1$H NMR(CDCl$_3$): δ8.72 (d, J=2.35, 1H), 8.53 (dd, J=1.26, 4.84, 1H), 7.77 (dt, J=1.77, 7.95, 1H), 7.27 (dd, J=4.80, 7.98, 1H), 5.59 (s,1H), 5.32 (s, 1H), 4.36 (s, 2H), 3.24 (t, J=7.07, 2H), 2.33 (t, J=7.98, 2H), 1.91 (m, 2H); $^{13}$C NMR(CDCl$_3$): δ175.26, 149.60, 147.97, 140.87, 133.90, 133.82, 123.59, 116.95, 46.75, 46.53, 31.16, 18.04; MS (m/e): 202 (M$^+$), 185, 174, 159, 147, 132, 119, 98, 70.

EXAMPLE 22
Preparation of 1-(2-hydroxyimino-2-pyridin-3-yl-ethyl)-pyrrolidin-2-one To 0.3 g (1.47 mmol) of 1-(2-oxo-2-pyridin-3-yl-ethyl)-pyrrolidin-2-one prepared from Example 20, 0.15 g (2.21 mmol) of hydroxylamine hydrochloride salt and 0.12 g of sodium sulfate were added in methanol/water (1.5:1). The mixture was reacted at 30~40° C. for 12~36 hours. Upon completion of the reaction, the reaction mixture was concentrated under reduced pressure, extracted with ethyl acetate for three times, washed with brine for two times, and dried over sodium sulfate. After concentrating under reduced pressure, it was purified by separation with silica gel column chromatography (chloroform/methanol (30:1~10:1)) to obtain 0.21 g (66% yield) of 1-(2-hydroxyimino-2-pyridin-3-yl-ethyl)-pyrrolidin-2-one as E/Z mixture (1.56:1).

$^1$H NMR(CDCl$_3$): δ12.61, 12.19 (2s, 1H), 9.11–7.31 (m, 4H), 4.75, 4.48 (2s, 2H), 3.35–3.31 (m, 2H), 2.39–2.27 (m, 2H), 1.95–1.85 (m, 2H); $^{13}$C NMR(CDCl$_3$): major isomer δ176.01, 151.00, 149.40, 147.47, 134.99, 130.94, 123.97, 47.75, 36.05, 36.05, 30.94, 18.00; minor isomer δ175.90, 150.10, 149.74, 127.64, 123.97, 47.17, 45.70, 31.06, 18.03; MS (m/e): 219 (M$^+$), 202, 146, 136, 98, 70.

EXAMPLE 23
Preparation of 1-(2-methoxyimino-2-pyridin-3-yl-ethyl)-pyrrolidin-2-one 0.3 g (1.47 mmol) of 1-(2-oxo-2-pyridin-3-yl-ethyl)-pyrrolidin-2-one prepared from Example 20 and 0.18 g (2.21 mmol) of methoxyamine hydrochloride salt were treated as described in Example 22 to obtain 0.24 g (70% yield) of 1-(2-methoxyimino-2-pyridin-3-yl-ethyl)-pyrrolidin-2-one as E/Z mixture (2.38:1).

$^1$H NMR(CDCl$_3$): δ8.96–7.29 (m, 4H), 4.63, 4.40 (2s, 2H), 4.05, 3.92 (2s, 3H0, 3.30, 3.23 (2t, J=7.07, 2H), 2.34–2.25 (m, 2H), 1.96–1.83 (m, 2H); $^{13}$C NMR(CDCl$_3$): major isomer δ175.42, 151.82, 150.69, 148.11, 136.04, 134.42, 123.63, 63.02, 47.41, 36.68, 30.75, 18.01; minor isomer δ175.35, 150.69, 150.29, 150.07, 129.68, 62.86, 46.98, 45.52, 30.92, 18.11; MS (m/e): 233 (M$^+$), 202, 150, 98, 70.

EXAMPLE 24
Preparation of 1-(2-propyn-2-yloxyimino-2-pyridin-3-yl-ethyl)-pyrrolidin-2-one 0.3 g (1.47 mmol) of 1-(2-oxo-2-pyridin-3-yl-ethyl)-pyrrolidin-2-one prepared from Example 20 and 0.24 g (2.21 mmol) of propargyloxyamine hydrochloride salt were treated as described in Example 22 to obtain 0.57 g (15% yield) of 1-(2-propyn-2-yloxyimino-2-pyridin-3-yl-ethyl)-pyrrolidin-2-one as E/Z mixture (1.80: 1).

$^1$H NMR(CDCl$_3$): δ8.98–7.30 (m, 4H), 4.85, 4.72 (2d, J=2.10, 2H), 4.65, 4.42 (s, 2H), 3.36, 3.27 (2t, J=7.11, 2H), 2.54–2.50 (m, 1H), 2.34–2.25 (m, 2H), 1.97–1.87 (m, 2H); $^{13}$C NMR(CDCl$_3$): major isomer δ175.40, 151.83, 150.86, 150.19, 136.15, 123.65, 79.63, 75.25, 62.49, 47.01, 45.51, 30.90, 18.15; minor isomer δ175.42, 153.53, 150.97, 148.28, 134.65, 79.13, 75.50, 62.80, 47.43, 36.93, 30.70, 18.04; MS (m/e): 219 (M$^+$), 203, 128, 78, 69.

EXAMPLE 25
Preparation of 1-(2-benzyloxyimino-2-pyridin-3-yl-ethyl)-pyrrolidin-2-one 0.3 g (1.47 mmol) of 1-(2-oxo-2-pyridin-3-yl-ethyl)-pyrrolidin-2-one prepared from Example 20 and 0.35 g (2.21 mmol) of benzyloxyamine hydrochloride salt were treated as described in Example 22 to obtain 0.14 g (31% yield) of 1-(2-benzyloxyimino-2-pyridin-3-yl-ethyl)-pyrrolidin-2-one as E/Z mixture (1.02:1).

$^1$H NMR(CDCl$_3$): δ8.96–7.28 (m, 9H), 5.27, 5.15 (2s, 2H), 4.63, 4.37 (2s, 2H), 3.23, 3.15 (2t, J=6.98, 2H), 2.29–2.22 (m, 2H), 1.89–1.81 (m, 2H); $^{13}$C NMR(CDCl$_3$): major isomer δ175.39, 150.63, 150.27, 148.17, 137.68, 136.10, 128.90, 128.81, 128.64, 128.53, 123.65, 77.17, 47.37, 45.58, 30.95, 18.11; minor isomer δ175.36, 152.16, 137.40, 134.47, 128.93, 128.81, 128.53, 128.38, 127.29, 77.17, 46.96, 36.86, 30.71, 17.99; MS (m/e): 309 (M$^+$), 292, 226, 202, 91.

EXAMPLE 26
Preparation of 1-[2-hydroxyimino-2-(1-methyl-1,2,5,6-tetrahydro-pyridin-3-yl)-ethyl]-pyrrolidin-2-one 0.2 g (0.91 mmol) of 1-(2-hydroxyimino-2-pyridin-3-yl-ethyl)-pyrrolidin-2-one prepared from Example 22 was treated as described in Example 12 to obtain 6 mg (61% yield) of 1-[2-hydroxyimino-2-(1-methyl-1,2,5,6-tetrahydro-pyridin-3-yl)-ethyl]-pyrrolidin-2-one.

$^1$H NMR(CDCl$_3$): δ6.38–6.36 (m, 1H), 4.40(s, 2H), 3.30–3.21 (m, 4H), 2.57 (t, J=5.78, 2H), 2.42–2.33 (m, 7H), 1.99–1.89 (m, 2H); $^{13}$C NMR(CDCl$_3$): δ175.16, 152.35, 130.88, 127.62, 53.43, 47.37, 45.80, 33.95, 31.14, 26.39, 18.01; MS (m/e): 237 (M$^+$), 220, 177, 135, 121, 98, 70.

EXAMPLE 27
Preparation of 1-[2-methoxyimino-2-(1-methyl-1,2,5,6-tetrahydro-pyridin-3-yl)-ethyl]-pyrrolidin-2-one 0.2 g (0.86 mmol) of 1-(2-methoxyimino-2-pyridin-3-yl-ethyl)-pyrrolidin-2-one prepared from Example 23 was treated as described in Example 12 to obtain 13 mg (12% yield) of 1-[2-methoxyimino-2-(1-methyl-1,2,5,6-tetrahydro-pyridin-3-yl)-ethyl]-pyrrolidin-2-one.

$^1$H NMR(CDCl$_3$): δ6.45, 6.12 (2m, 1H), 4.36, 4.13 (2s, 2H), 3.89, 3.84 (2s, 3H), 3.33, 3.25 (m, 2H), 2.41–2.32 (m, 7H), 2.02–1.97 (m, 2H); $^{13}$C NMR(CDCl$_3$): δ174.76, 152, 131.03, 129.13, 62.37, 53.76, 51.86, 47.14, 46.33, 34.43, 31.01, 27.29, 17.89; MS (m/e): 251 (M$^+$), 177, 135, 121, 98, 70.

EXAMPLE 28
Preparation of 1-[2-(1-methyl-1,2,5,6-tetrahydro-pyridin-3-yl)-2-propyn-2-yloxyimino-ethyl]-pyrrolidin-2-one 0.2 g (0.78 mmol) of 1-(2-propyn-2-yloxyimino-2-pyridin-3-yl-ethyl)-pyrrolidin-2-one prepared from Example 24 was treated as described in Example 12 to obtain 25 mg (23% yield) of 1-[2-(1-methyl-1,2,5,6-tetrahydro-pyridin-3-yl)-2-propyn-2-yloxyimino-ethyl]-pyrrolidin-2-one.

$^1$H NMR(CDCl$_3$): δ6.54–6.51(m, 1H), 4.71(d, J=2.36, 2H), 4.38 (s, 2H0, 3.28 (t, J=14.7, 2H), 3.17 (d, J=1.74, 2H), 2.52–2.31 (m, 10H), 2.01–1.93 (m, 2H); $^{13}$C NMR(CDCl$_3$): δ174.87, 153.86, 130.87, 130.21, 79.85, 74.94, 62.23, 53.66, 51.80, 47.25, 46.32, 34.65, 31.05, 37.35, 17.93.

EXAMPLE 29
Preparation of 1-[2-benzyloxyimino-2-(1-methyl-1,2,5,6-tetrahydro-pyridin-3-yl)-ethyl]-pyrrolidin-2-one 0.2 g (0.65 mmol) of 1-(2-benzyloxyimino-2-pyridin-3-yl-ethyl)-pyrrolidin-2-one prepared from Example 25 was treated as described in Example 12 to obtain 77 mg (73% yield) of 1-[2-benzyloxyimino-2-(1-methyl-1,2,5,6-tetrahydro-pyridin-3-yl)-ethyl]-pyrrolidin-2-one as E/Z mixture (4.24:1).

$^1$H NMR(CDCl$_3$): δ7.34–7.32 (m, 5H), 6.45, 6.15 (2m, 1H), 5.13, 5.07 (2s, 2H), 4.38, 4.12 (2s, 2H), 3.23–3.12 (m, 4H), 2.50–2.26 (m, 9H), 1.93–1.85 (m, 2H); $^{13}$C NMR (CDCl$_3$): major isomer δ174.77, 152.88, 137.75, 131.15, 129.33, 128.82, 128.76, 128.40, 76.96, 53.78, 51.85, 47.13, 46.36, 45.97, 34.66, 30.98, 27.32, 17.86; minor isomer δ175.15, 152.34, 138.20, 130.11, 129.84, 128.94, 128.67, 128.13, 76.70, 56.44, 51.39, 47.05, 45.18, 31.21, 26.56, 18.13; MS (m/e): 327 (M$^+$), 220, 121, 98, 70.

EXAMPLE 30
Preparation of 1-[3-(1-methyl-1,2,5,6-tetrahydro-pyridin-3-yl)-propyn-2-yl]-pyrrolidin-2-one 0.61 g (1.78 mmol) of 1-(3-pyridin-3-yl-propyn-2-yl)-pyrrolidin-2-one prepared from Example 1was treated as described in Example 12 to obtain 0.32 g (83% yield) of 1-[3-(1-methyl-1,2,5,6-tetrahydro-pyridin-3-yl)-propyn-2-yl]-pyrrolidin-2-one.

$^1$H NMR(CDCl$_3$): δ6.13–6.10 (m, 1H), 4.27 (s, 2H), 3.48 (t, J=7.14, 2H), 2.95–2.93 (m, 2H), 2.48 (t, J=7.14, 2H), 2.42–2.24 (m, 7H), 2.08–2.03 (m, 2H); $^{13}$C NMR(CDCl$_3$): δ174.80, 133.01, 119.33, 83.46, 82.23, 57.45, 51.18, 46.73, 45.84, 33.01, 31.15, 26.64, 17.94; MS(m/e): 218 (M$^+$), 190, 135, 70.

Measurement of Drug Effect

In order to demonstrate the availability of tetrahydropyridine derivatives of formula 1 according to the present invention, the activity of the representative compounds as muscarinic acetylcholine receptor agonists were examined.

Efficacy of novel anti-dementia candidate substances acting on muscarinic receptors is demonstrated by primarily investigating the affinity of the substances for the receptors using the muscarinic receptor affinity screening test, and then analyzing the function of the substances (a muscarinic agonist/antagonist) by [$^3$H]-oxotremorine affinity screening test, organ bath method using avulsed ileum of Guinea pig, and phosphoinositide turnover measurement. The candidate substances thus screened are finally accessed for their efficacy using passive avoidance test, which is an in vivo test on learning and memorizing, and general pharmacological/behavioral measurements, and the like.

In Vitro Affinity Screening Test to Screen Muscarinic Receptor Agonist

[$^3$H]-N-methyl-scopolamine ([$^3$H]-NMS) Affinity Screening Test

In order to exclude the interaction between subtypes, human recombinant muscarinic receptor subtypes 1, 2 and 3 expressed in CHO cells (M1, M2 and M3, Biosignal, Canada) were purchased and used as receptor sources. [$^3$H]-N-methyl-scopolamine (NEN, NET-636) was used as radioisotope labeled ligands, and atropine was used for the measurement of the non-specific binding ability. About 10 kinds of experimental apparatuses including Liquid Scintillation Counter (MicroBeta 1450 plus), Inotech cell harvester (96-well) were used.

In order to determine the effect of each compound on M1 and M2 receptors, the compounds were reacted with the receptors using radioisotope labeled ligands. After the reaction, the excess unbound ligands were removed by filtering with a glass fiber filter. The amount of radioisotopes remaining on the washed filter plate was then measured to quantify the binding reaction between the receptors and the ligands and, from the result, the affinity of the drugs for the receptors was determined.

The freeze-stored receptors at −70° C. were suspended in test buffer solutions and then the screening test (BioRad protein) was carried out to determine the optimum concentration of the proteins. Thereafter, 50 μL of hot-ligands and 10 μL of test drugs were added to 96-well plate and 100 μL of 50 mM TRIS buffer (pH 7.2) containing 10 mM $MgCl_2$ and 1 mM EDTA was added as a test buffer. The final volume of the reaction was 0.25 mL. The reaction was initiated by adding 100 μL of the diluted receptor suspension, and continued for 60 minutes on a shaking incubator at 27° C. This test was repeated four times. After 60 minutes, the reaction was terminated by adding cold TRIS buffer (0.5 mL, pH 7.4). The excess unbound radioisotopes were removed from the reaction mixture using Inotech cell harvester system. After washing the mixture, the radioactivity detected by the filter mat was measured using Liquid Scintillation Counter. As primary stage of the efficacy screening, the drugs at two concentrations (1 μM, 10 μM) were screened for their affinity for the receptors. As secondary stage, drugs showing remarkable efficacies were determined at the lower concentrations. Finally, $IC_{50}$ values were calculated at the gradient of 10 concentrations. The test drugs were diluted sequentially for the required concentrations by dissolving them in dimethylsulfoxide (DMSO). The final reaction concentration 1% of dimethylsulfoxide did not affect the binding reaction. From the saturation affinity screening test, $K_d$ and $B_{max}$ values, and $IC_{50}$ or $K_i$ values of each test drugs were calculated by observing the non-linear regression using prism (Graphpad software Inc.,USA).

In the equilibrium affinity screening test, [$^3$H]-N-methyl-scopolamines at the gradient of 12 concentrations were used for the measurement of the binding ability ($IC_{50}$). In the competition screening test, 1 nM of [$^3$H]-N-methyl-scopolamines, and the reference drugs at the gradient of 10 concentrations were used for the measurement. 4-DAMP-methyliodide, Pirenzepine, p-F-hexahydro-sila-defenidol, Methoctramine, and the like were used as reference drugs. [$^3$H]-oxotremorine-M ([$^3$H]-Oxo-M) Affinity Screening Test The experimental principle was the same as [$^3$H]-NMS affinity screening test. The present experiment was carried out in order to identify the pharmacological functions (an agonist or antagonist) of the compounds showing high affinity in [$^3$H]-NMS affinity screening test. The functions of the compounds may be determined by carrying out both of [$^3$H]-NMS and [$^3$H]-Oxo-M (oxotremorine) affinity screening tests to measure their respective $IC_{50}$ values and calculating ratios (NMS/Oxo-M) of the measured $IC_{50}$ values. Generally, the compounds are evaluated as muscarinic receptor full agonists when the ratio is greater than 180, as partial agonists when the ratio is from 14 to 130, and as antagonists when the ratio is from 0.2 to 1.9.

Preparation of Brain Membrane

Synapse membranes for binding assay of Oxo-M binding receptor of muscarinic receptors were directly prepared and used in the laboratory as follows: male Sparague-Dawley rats (supplied from Laboratory Animal Center of Korea Research Institute of Chemical Technology, 250 to 300 g) were sacrificed by decapitation. The brain tissues were immediately removed from and the forebrain was obtained, which was sectioned into small pieces. After adding 10-fold amount of ice-cooled solution of sucrose (0.32M), the sectioned forebrain was homogenized using Teflon-glass homogenizer (Contorque, Eberbach) at 10 strokes and 500 rpm, centrifuged at 1000 g for 15 minutes, and then the supernatant was again centrifuged at 17000 g for 20 minutes. The pellet was stored at −20° C. and then used.

Before the pellet was used at this assay, it was suspended in 10 mL of 20 mM HEPES buffer (pH 7.4), again centrifuged at 17000 g for 15 minutes and then washed. Finally, the washed membrane was diluted in ice-cooled 20 mM HEPES buffer (pH 7.4) to the final concentration of 1:100 (wet wt/v) and used at this assay. All test samples were tested four times, and 20 mM HEPES buffer (pH 7.4) was used as a buffer for screening test. The final volume of reaction was 1 mL, and 24-well plate (costar 24-well) was used. 50 μL of hot-ligand (Oxo-M 5 nM) and 10 μL of test drugs were included therein, and the reaction was initiated by adding 750 μL of synapse membrane and continued at 30° C. for 40 minutes on the shaking incubator. 2 μM atropine was used for non-specific binding in all tests. After completion of the reaction, the receptor binding ligands and non-binding ligands were separated by using Inotech cell harvester (24-channels, Inotech, Switzerland) and filtering under reduced pressure (10×ice-cooled saline) with Wallac GF/C filter (pre-immersed in 0.05% polyethylene imine). The radioactivity of the receptor binding ligands was detected by Liquid Scintillation Counter (MicroBeta Plus, Wallac, Finland).

The test drugs were diluted sequentially for the required concentrations by dissolving them in dimethylsulfoxide (DMSO) and used in the test. The final reaction concentration 1% of DMSO did not affect the binding reaction. From the saturated affinity screening test, $K_d$ and $B_{max}$ values, and $IC_{50}$ or $K_i$ values of respective test drugs were calculated by observing the non-linear regression using prism (Graphpad software Inc., USA). The saturated affinity screening test was carried out in the range of 0.1 to 10 nM of [$^3$H]-Oxo-M ligand as described above.

The following table 1 illustrates the affinity of representative compounds of the present invention for muscarinic receptor measured by binding of [$^3$H]-N-methyl scopolamine ([$^3$H]-NMS) and [$^3$H]-oxotremorine ([$^3$H]-Oxo-M) to cortex receptor of rats. The affinity was expressed as inhibition (%), and $IC_{50}$ (μM) that is the concentration of the substrate compound to inhibit 50% of the specific binding of [$^3$H]-NMS and [$^3$H]-Oxo-M to the receptor, and compared with arecoline as a reference compound.

TABLE 1

Affinity of Representative Compounds for Muscarinic Receptors (inhibition (%) and $IC_{50}$ (nM))

| | M1 | | | | | M2 |
|---|---|---|---|---|---|---|
| Compound | NMS (10 μM) | $IC_{50}$(μM) | Oxo-M (1 μM) | $IC_{50}$ (μM) | NMS/ Oxo-M | NMS (1 μM) |
| Example 16 | 39.5 | 17.43 | 92.4 | 0.074 | 236 | 22.6 |
| Example 18 | 42.9 | 13.45 | 75.3 | 0.381 | 35 | 26.8 |
| Example 24 | 0 | 100.00 | 58.0 | 0.327 | 306 | 0 |
| Example 26 | 87.6 | 3.63 | 96.9 | 0.00089 | 4078 | 94.1 |

TABLE 1-continued

Affinity of Representative Compounds for Muscarinic Receptors (inhibition (%) and IC$_{50}$ (nM))

| | M1 | | | | | M2 |
|---|---|---|---|---|---|---|
| Compound | NMS (10 μM) | IC$_{50}$(μM) | Oxo-M (1 μM) | IC$_{50}$ (μM) | NMS/ Oxo-M | NMS (1 μM) |
| Example 29 | 0 | 79.17 | 78.4 | 0.163 | 486 | 0 |
| Example 30 | 58.5 | 10.83 | 96.6 | 0.014 | 774 | 42.3 |
| Arecoline | 0 | 87.10 | 85.5 | 0.14 | 622 | |

As shown in Table 1, the novel compounds according to the invention show high affinity for muscarinic receptors and selectivity for subtype receptors. The compounds also show higher efficacies and effects as agonists which was determined by the ratio between inhibition of the compounds to N-methyl scopolamine (NMS) and the inhibition of the compounds to oxotremorine (Oxo-M).

What is claimed is:

1. A tetrahydropyridine compound of formula 1,

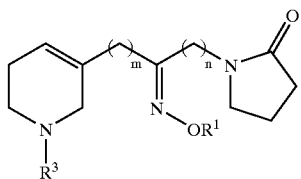

wherein m is 0 or 1, n is 1 or 2, $R^1$ is hydrogen, $C_{1-4}$ alkyl, $C_{2-4}$ alkynyl or aryl, and $R^3$ is $C_{1-4}$ alkyl;

and pharmaceutically acceptable salts thereof.

2. The compound of the formula 1 according to claim 1, wherein $R^1$ is hydrogen, methyl, propargyl or benzyl and $R^3$ is methyl.

3. The compound of the formula 1 according to claim 1, selected from:

1-[3-benzyloxyimino-3-(1-methyl-1,2,5,6-tetrahydro-pyridin-3-yl)-propyl]-pyrrolidin-2-one,
1-[2-benzyloxyimino-3-(1-methyl-1,2,5,6-tetrahydro-pyridin-3-yl)-propyl]-pyrrolidin-2-one,
1-[3-methoxyimino-3-(1-methyl-1,2,5,6-tetrahydro-pyridin-3-yl)-propyl]-pyrrolidin-2-one,
1-[2-methoxyimino-3-(1-methyl-1,2,5,6-tetrahydro-pyridin-3-yl)-propyl]-pyrrolidin-2-one,
1-[3-hydroxyimino-3-(1-methyl-1,2,5,6-tetrahydro-pyridin-3-yl)-propyl]-pyrrolidin-2-one,
1-[2-hydroxyimino-3-(1-methyl-1,2,5,6-tetrahydro-pyridin-3-yl)-propyl]-pyrrolidin-2-one,
1-[3-(1-methyl-1,2,5,6-tetrahydro-pyridin-3-yl)-3-propyn-2-yloxyimino-propyl]-pyrrolidin-2-one,
1-[3-(1-methyl-1,2,5,6-tetrahydro-pyridin-3-yl)-2-propyn-2-yloxyimino-propyl]-pyrrolidin-2-one,
1-[2-hydroxyimino-2-(1-methyl-1,2,5,6-tetrahydro-pyridin-3-yl)-ethyl]-pyrrolidin-2-one,
1-[2-methoxyimino-2-(1-methyl-1,2,5,6-tetrahydro-pyridin-3-yl)-ethyl]-pyrrolidin-2-one,
1-[2-(1-methyl-1,2,5,6-tetrahydro-pyridin-3-yl)-2-propyn-2-yloxyimino-ethyl]-pyrrolidin-2-one,
1-[2-benzyloxyimino-2-(1-methyl-1,2,5,6-tetrahydro-pyridin-3-yl)-ethyl]-pyrrolidin-2-one, and
pharmaceutically acceptable salts thereof.

4. A process for preparing a tetrahydropyridine derivative of formula 1,

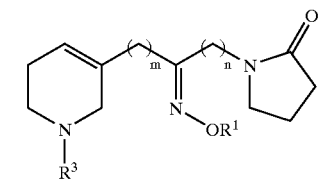

wherein m, n, $R^1$ and $R^3$ are as defined in claim 1, comprising:

i) performing a condensation reaction with a compound of formula 5,

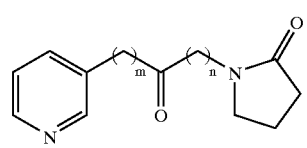

wherein m and n are as defined in claim 1, and $R^1ONH_2$.HCl, wherein $R^1$ is as defined in claim 1, to obtain a compound of formula 8,

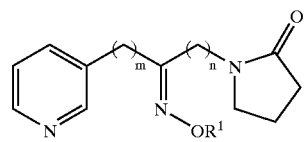

wherein m, n and $R^1$ are as defined in claim 1; and ii) reacting the resulting compound of formula 8 with an alkyl iodide to form an alkyl pyridinium salt, and then reducing the salt to obtain the compound of formula 1.

5. The process according to claim 4, wherein a compound of formula 5a, which is the compound of formula 5 wherein m is 0 and n is 1,

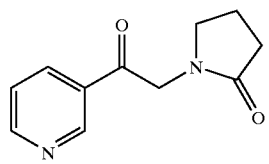

is obtained by an alkylation of halogen at the 3-position of a pyridine of formula 2,

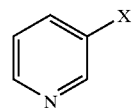

wherein X is iodine, bromine or chlorine, followed by a coupling reaction with 2-(oxo-pyrrolidin-1-yl)-acetonitrile or 2-(oxo-pyrrolidin-1-yl)-acetic acid ethyl ester.

6. The process according to claim 4, wherein a compound of formula 5a, which is the compound of formula 5 wherein m is 0 and n is 1,

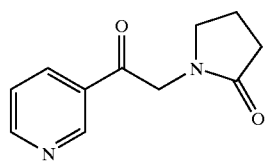
5a is synthesized by a coupling reaction of a compound of formula 2a

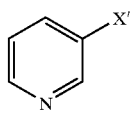
2a wherein X' is B(OR)$_2$, B$^-$(OR)$_3$Li$^+$ or SnBu$_3$ and R is hydrogen or C$_{1-4}$ alkyl, with 1-(2-bromoallyl)-pyrrolidin-2-one, followed by an ozonolysis.

7. The process according to claim 4, wherein compounds of formula 5b and 5c, which are the compounds of formula 5 wherein m=0 and n=2, and m=1 and n=1, respectively,

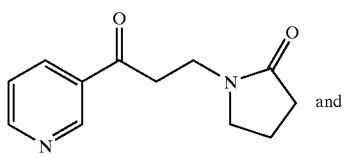
5b and

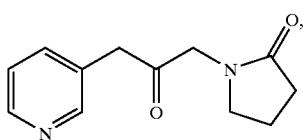
5c are prepared by performing a coupling reaction with the compound of formula 6

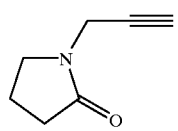
6 and a compound of formula 2,

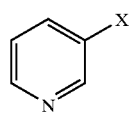
2 wherein X is iodine, bromine or chlorine, to obtain the alkyne compound of formula 7

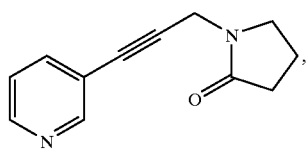
7 and then performing a hydration reaction into the alkyne compound of formula 7.

8. A compound selected from the group consisting of:

1-(3-benzyloxyimino-3-pyridin-3-yl-propyl)-pyrrolidin-2-one, 1-(2-benzyloxyimino-3-pyridin-3-yl-propyl)-pyrrolidin-2-one, 1-(3-methoxyimino-3-pyridin-3-yl-propyl)-pyrrolidin-2-one, 1-(2-methoxyimino-3-pyridin-3-yl-propyl)-pyrrolidin-2-one, 1-(3-hydroxyimino-3-pyridin-3-yl-propyl)-pyrrolidin-2-one, 1-(2-hydroxyimino-3-pyridin-3-yl-propyl)-pyrrolidin-2-one, 1-(3-propyn-2-yloxyimino-3-pyridin-3-yl-propyl)-pyrrolidin-2-one, 1-(2-propyn-2-yloxyimino-3-pyridin-3-yl-propyl)-pyrrolidin-2-one, 1-(2-hydroxyimino-2-pyridin-3-yl-ethyl)-pyrrolidin-2-one, 1-(2-methoxyimino-2-pyridin-3-yl-ethyl)-pyrrolidin-2-one, 1-(2-propyn-2-yloxyimino-2-pyridin-3-yl-ethyl)-pyrrolidin-2-one, 1-(2-benzyloxyimino-2-pyridin-3-yl-ethyl)-pyrrolidin-2-one, and pharmaceutically acceptable salts thereof.

9. A compound selected from the group consisting of 1-[3-(1-methyl-1,2,5,6-tetrahydro-pyridin-3-yl)-propyn-2-yl]-pyrrolidin-2-one and pharmaceutically acceptable salts thereof.

10. A pharmaceutical composition which comprises a compound of formula 1 or a pharmaceutically acceptable salt thereof according to claim 1, as an active ingredient, and a pharmaceutically acceptable carrier.

11. A pharmaceutical composition which comprises a compound of formula 1 or a pharmaceutically acceptable salt thereof according to claim 2, as an active ingredient, and a pharmaceutically acceptable carrier.

12. A pharmaceutical composition which comprises a compound of formula 1 or a pharmaceutically acceptable salt thereof according to claim 3, as an active ingredient, and a pharmaceutically acceptable carrier.

13. A pharmaceutical composition which comprises a compound on a pharmaceutically acceptable salt thereof according to claim 8, as an active ingredient, and a pharmaceutically acceptable carrier.

14. A pharmaceutical composition which comprises a compound on a pharmaceutically acceptable salt thereof according to claim 9, as an active ingredient, and a pharmaceutically acceptable carrier.

* * * * *